under_ United States Patent [19]

Kohayakawa

[11] Patent Number: 5,523,809
[45] Date of Patent: Jun. 4, 1996

[54] EYE REFRACTION MEASURING APPARATUS INCLUDING OPTICAL PATH SEPARATING MEMBER LIGHT BEAM SEPARATING MEMBER, AND/OR LIGHT DIAMETER CHANGING MEANS

[75] Inventor: Yoshimi Kohayakawa, Yokohama, Japan

[73] Assignee: Canon Kabushiki Kaisha, Tokyo, Japan

[21] Appl. No.: 111,442

[22] Filed: Aug. 24, 1993

[30] Foreign Application Priority Data

Aug. 25, 1992 [JP] Japan ................................. 4-250689
Nov. 9, 1992 [JP] Japan ................................. 4-323673
Feb. 25, 1993 [JP] Japan ................................. 5-061167

[51] Int. Cl.⁶ ........................................................... A61B 3/10
[52] U.S. Cl. ........................... 351/211; 351/214; 351/221
[58] Field of Search ..................................... 351/205, 211, 351/221, 214, 206; 354/62

[56] References Cited

U.S. PATENT DOCUMENTS

| 4,021,102 | 5/1977 | Iizuka | 351/211 |
| 4,162,828 | 7/1979 | Trachtman | 351/211 |
| 4,372,655 | 2/1983 | Matsumura et al. | 351/211 X |
| 4,376,573 | 3/1983 | Matsumura et al. | 351/211 |
| 4,744,648 | 5/1988 | Kato et al. | 351/211 |
| 4,761,070 | 8/1988 | Fukuma | 351/211 |

*Primary Examiner*—William L. Sikes
*Assistant Examiner*—Hung Xuan Dang
*Attorney, Agent, or Firm*—Fitzpatrick, Cella, Harper & Scinto

[57] ABSTRACT

An eye refraction measuring apparatus for ophtalmology can separate a projected light beam from a reflected light beam from an eye fundus without using a special optical member such as an apertured-mirror. As a result, the constitution of the apparatus can be simplified and miniturized, a the measurable and measurement precision can be the improved, distribution of refractivity of a pupil in radial directions can be measured, and a small pupil and a cloudy eye can be easily measured.

14 Claims, 7 Drawing Sheets

EYE REFRACTION MEASURING
APPARATUS INCLUDING OPTICAL PATH
SEPARATING MEMBER LIGHT BEAM
SEPARATING MEMBER, AND/OR LIGHT
DIAMETER CHANGING MEANS

BACKGROUND OF THE INVENTION

1. Field of the Invention

The present invention relates to an eye refraction measuring apparatus which is to be used in an ophthalmic clinic and in an optician's store.

2. Related Background Art

A conventional auto refractometer which uses an optical position sensor has the advantage that refractivity in respective meridian directions can be simultaneously measured. Such an auto refractometer employs a special optical member such as an apertured mirror which is positioned so as to be conjugated with a pupil, and separates a projected light beam from a reflected light beam by using the optical member. On the other hand, a method of separation in which a member for dividing intensity of the light beam such as a half mirror is used has been disclosed, for example, in U.S. Pat. No. 4,162,828.

As the structure is complicated, optical systems in the above-mentioned conventional auto refractometer which separates the projected light beam from the reflected light beam by means of the apertured mirror or the like are difficult to miniaturize. Furthermore, as separation has to be performed on a pupil, sometimes an eye with an opaque pupil can not be measured. Though such problems can be solved by the method disclosed in U.S. Pat. No. 4,162,828, improvement of the measurable range and precision of an apparatus employing this method has a certain limit. For the light beam blurs on a detector except for emmetropia.

Generally, the distribution of refractivity is not uniform in a pupil. The above-mentioned conventional auto refractometers are not suitable to measure the eye with such a non-uniform distribution.

Further, the method employing a half mirror or the like should be improved so as to be applied to measurement of a pupil having a small diameter.

SUMMARY OF THE INVENTION

An object of the present invention is to provide an eye refraction measuring apparatus which can measure an eye having non-uniform refracting in the pupil.

Another object of the present invention is to provide an eye refraction measuring apparatus which can separate a projected light beam from a reflected light beam from an eye fundus without using a special optical member, wherein this eye refraction measuring apparatus can have a simple and small constitution and a wide measurable range and high precision.

Another object of the present invention is to provide an eye refraction measuring apparatus which can separate a projected light beam from a reflected light beam from an eye fundus without using a special optical member, wherein this eye refraction measuring apparatus can have a simple and small constitution and measure the distribution of refractivity even in the radial direction on a pupil.

Still another object of the present invention is to provide an eye refraction measuring apparatus which can separate a projected light beam from a reflected light beam from an eye fundus without using a special optical member, wherein this eye refraction measuring apparatus can have a simple and small constitution and can be easily used to measure an eye with small pupil or which has some opacity.

Other objects of the present invention will be clearly understood from the following description of the embodiments.

DESCRIPTION OF THE PREFERRED EMBODIMENTS

The present invention will be described in detail with reference to the drawings showing the embodiments of the present invention.

Figure 1:
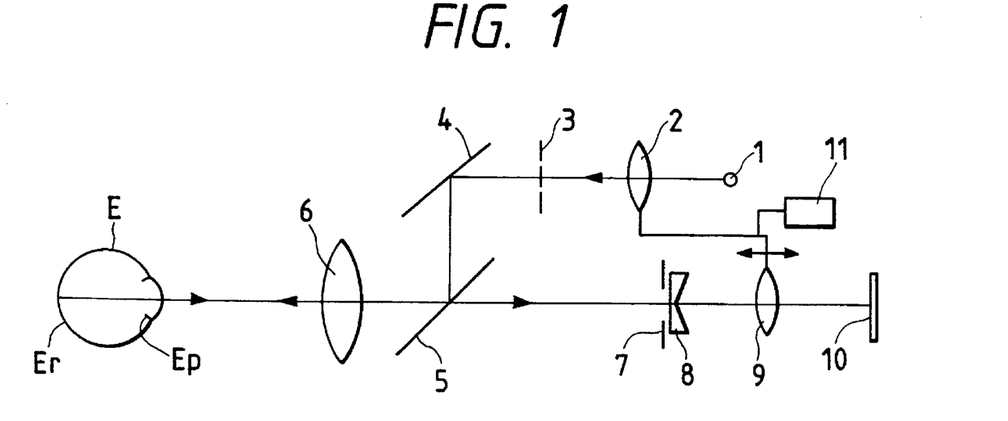
FIG. 1 is a block diagram of the first embodiment.

FIG. 1 shows the first embodiment. On a light path from a light source 1 (point light source such as an LED) to an eye E to be examined, there are arranged: a lens 2; a ring aperture stop 3 having a ring-shaped aperture portion 3a shown in FIG. 2; a mirror 4; a half mirror 5; and an object lens 6, which together comprise a projection optical system.

Also, on an optical path behind the half mirror 5, there are arranged: a center aperture stop 7; an inversed conical prism 8; a lens 9; and an image pick-up element 10 consisting of a two-dimensional CCD, together comprising a light-receiving optical system.

Figure 2:
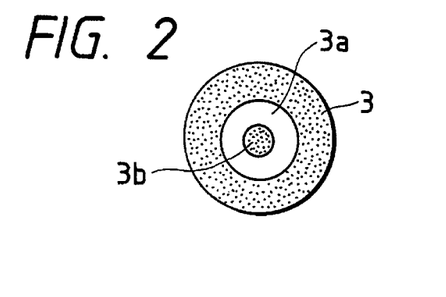
FIG. 2 is a front view of a ring aperture stop.

In this case, the shielding portion 3b at the center of the ring aperture stop 3 shown in FIG. 2 is positioned on an optical axis, and both the ring aperture stop 3 and the center aperture stop 7 are located at conjugate points with respect to a pupil Ep. Also, the point light source 1 is located at a conjugate point with respect to the image pick-up element 10. The lenses 2 and 9 are moved together along the optical axses by an interlocking mechanism 11.

A light beam from the light source 1 passes through the lens 2 and the ring aperture stop 3, and is reflected by the mirror 4 and the half mirror 5 to spotlight an eye fundus Er through the object lens 6. The reflected light beam from the eye fundus Er passes through the object lens 6, the half mirror 5, the center aperture stop 7, the prism 8 and the lens 9 to be formed on the image pick-up element 10 as a ring-shaped reflected light beam image Pr shown in FIG. 3. The reflected light beam image Pr is brought into focus by moving the lenses 2 and 9 together along an optical axis by the interlocking mechanism 11. At the focused position of the lenses 2 and 9, image signals from the image pick-up element 10 are input to a computer (not shown) to analyze the shape of the reflected light beam image Pr and obtain the eye refractivity.

Figure 3:
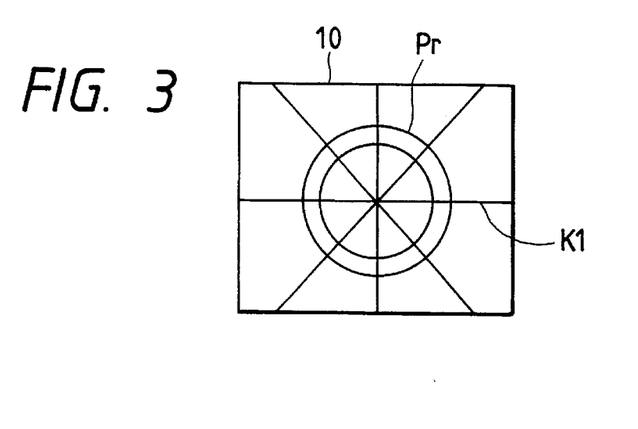
FIG. 3 is an explanatory view of a reflected light beam image formed on an image pick-up element.

The size of the reflected light beam image Pr varies according to the refractivity of the eye E to be examined and the positions of the lenses 2 and 9. The shape of the reflected light beam image Pr becomes elliptical if the eye E to be examined is astigmatic. The refractivity of the eye sphere is calculated on the basis of the size of the reflected light beam image Pr and the positions of the lenses 2 and 9, while the degree of astigmatism and direction of astigmatism are calculated on the basis of ellipticity and orientation of the ellipse.

For focusing, the signals from such as the horizontal meridian K1 on the image pick-up element 10, are monitored while the lenses 2 and 9 are moved. When they are not in-focus, the signals shown as signals S1 in FIG. 4, have broad and low peaks. While in focus, they have narrow width and high as shown as signal 52. After focusing, all the light receiving signals of the image pick-up element 10 are input to the computer to obtain eye refraction values including those of astigmatism.

In FIG. 1, the ring aperture stop 3 and the center aperture stop 7 can be exchanged. In this case, though the reflected light beam from the cornea can be prevented from being incident on the image pick-up element 10, the reflected light beam from the object lens 6 can not be shielded and can be incident on the image pick-up element 10. Accordingly, a countermeasure such that the light beam is deviated from the optical axis must be taken.

Figure 5:
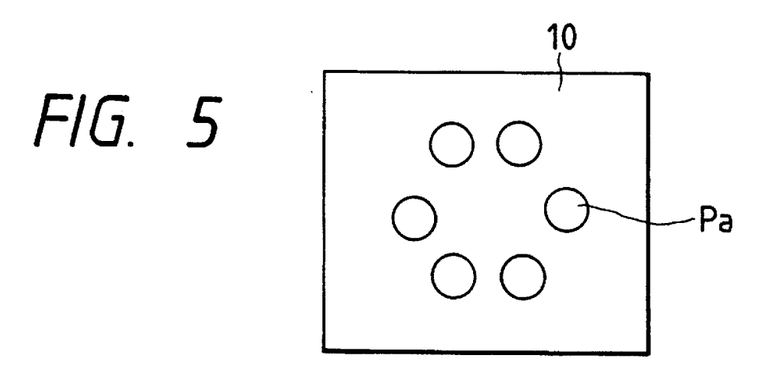
FIG. 5 is an explanatory view of reflected light beam images formed on the image pick-up element.

Also, the inversed conical prism 8 may be replaced by a prism consisting of six wedge prisms. In this case, the reflected light beams from the eye fundus Er are formed as an image on the image pick-up element 10 as reflected light beam images Pa, which are six small circles shown in FIG. 5. Refraction values for ophtalmology including those of astigmatism can be obtained on the basis of the positions of these reflected light beam images Pa.

Figure 6:
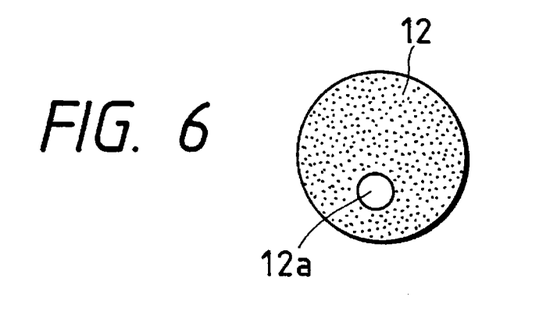
FIG. 6 is a front view of an eccentric diaphragm.

Furthermore, the ring aperture stop 3 can be replaced by an eccentric diaphragm 12 having an aperture 12a at a position eccentric with respect to the optical axis as shown in FIG. 6. In this case, the light beam from the light source 1 passes through the aperture 12a of the eccentric diaphragm 12 and part of the pupil Ep to be projected on the eye fundus Er, wherein the blur in the projection optical system caused by the diopter of the eye E to be examined is small.

Accordingly, the lens 2 of the projection optical system may not be moved, and only the lens 9 of the light receiving optical system is driven for focusing.

Figure 7:
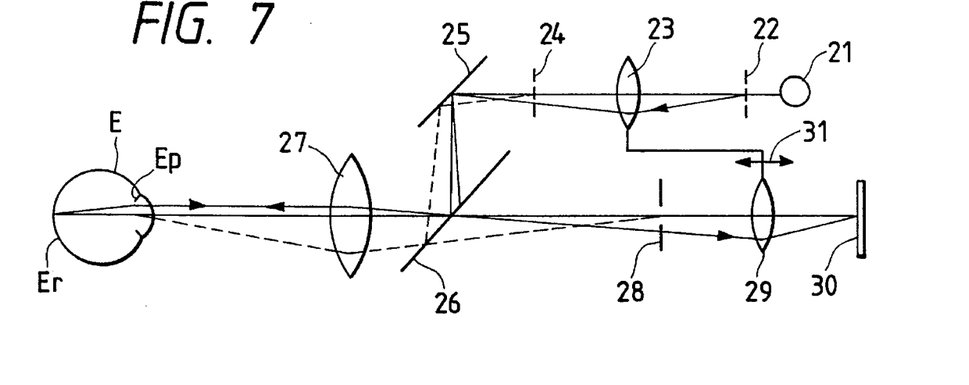
FIG. 7 is a block diagram of the second embodiment.

FIG. 7 is a block diagram of the second embodiment. On an optical path from a light source 21 to the eye E to be examined, there are arranged: a ring aperture stop 22; a lens 23; a ring aperture stop 24 which is same as that shown in FIG. 2; a mirror 25; a half mirror 26; and an object lens 27. On an optical path behind the half mirror 26, there are arranged: a center aperture stop 28; a lens 29; and a two-dimensional image pick-up element 30. The lenses 23 and 29 are simultaneously moved along optical axes by an interlocking mechanism 31. The ring aperture stop 22 and the two-dimensional image pick-up element 30 are positioned at conjugate positions with respect to the eye fundus Er, while the ring aperture stop 24 and the center aperture stop 28 are positioned at conjugate positions with respect to the pupil.

The light beam from the light source 21 passes through the ring aperture stop 22, the lens 23 and the ring aperture stop 24, and is reflected by the mirror 25 and the half mirror 26 to illuminate the eye fundus Er through the object lens 27 with ring-shaped light. The reflected light beam from the eye fundus Er passes through the object lens 27, the half mirror 26, the center aperture stop 28 and the lens 29 to be formed on the image pick-up element 30 as a ring-shaped reflected light beam image Pr shown in FIG. 8.

The lenses 23 and 29, which are mechanically linked, are moved along the optical axes by the interlocking mechanism 31 for focusing. After completion of focusing, the signals from the image pick-up element 30 are input to a computer (not shown) in order to analyze the shape of the reflected light beam image Pr. Using the information of the shape and the positions of the lenses 23 and 29 and refraction values including those of astigmatism are calculated.

Figure 4:
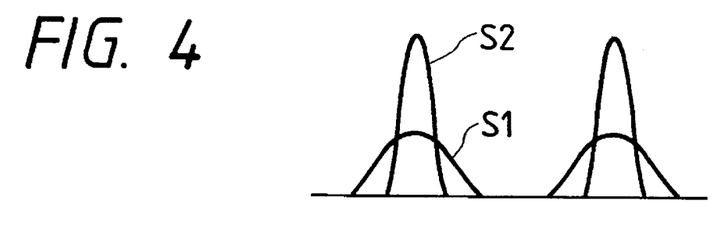
FIG. 4 is an explanatory view of light-receiving signals on a horizontal meridian of the image pick-up element.
Figure 8:
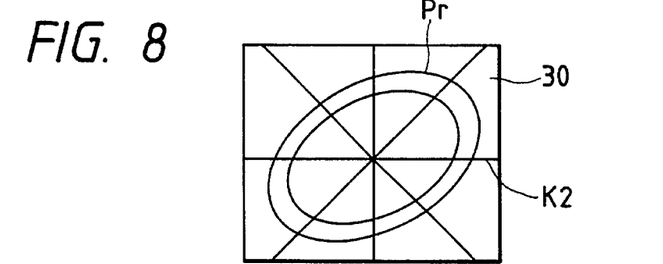
FIG. 8 is an explanatory view of a reflected light beam image formed on the image pick-up element.

The focusing operation may be performed either by determining the sharpness of the ring image Pr as shown in FIG. 4, or by determining the size of the ring image Pr since the ring image Pr has the same size as the ring aperture of the stop 22 when it is conjugate to the fundus Er. In this case, the interlocking mechanism 31 scans the optical axes with the lenses 23 and 29 while the light receiving signals on the horizontal meridian K2 on the image pick-up element 30 shown in FIG. 8 are monitered by the computer. Thus, the positions of the lenses 23 and 29 which mates the reflected light beam image Pr the same size as the aperture 22a of the ring aperture stop 22 are determined. After shifting the lenses 23 and 29 to these positions, respectively, the image signals are input to the computer (not shown) to perform a calculation.

In this embodiment, even when the diameter of the pupil Ep is smaller than that of the aperture of the center aperture stop 28, the size of the ring of the reflected light beam image Pr which is received by the image pick-up element 30 remains the same. But, the ellipticity of the reflected light beam image Pr varies according to the size of the pupil Ep. Accordingly, when the eye E to be examined has a small pupil, the measured refraction values must be compensated for by measuring the pupil size in order to obtain exact data on the stigmatism of the eye.

In the above-mentioned embodiment of an eye refractometer using an image sensor such as CCD, a one-dimensional optical position sensor may be used for an optometer.

Figure 9:
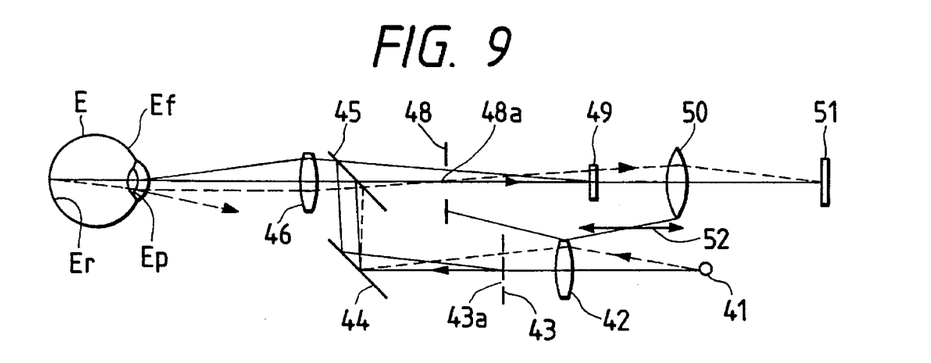
FIG. 9 is a block diagram of the third embodiment.

FIG. 9 is a schematic view of the third embodiment. On an optical path from a light source 41 such as an LED, to the eye E to be examined, there are arranged: a lens 42; a ring aperture stop 43, which is the same as that shown in FIG. 2 and has a ring aperture 43a; a mirror 44; a half mirror 45; and an object lens 46. On an optical path behind the half mirror 45, there are arranged: a center aperture stop 48; a light beam separating member 49; a lens 50; and a CCD image pick-up element 51. Also, an interlocking mechanism 52 is provided to simultaneously move the lenses 42 and 50 and the center aperture stop 48 together.

Figure 10:
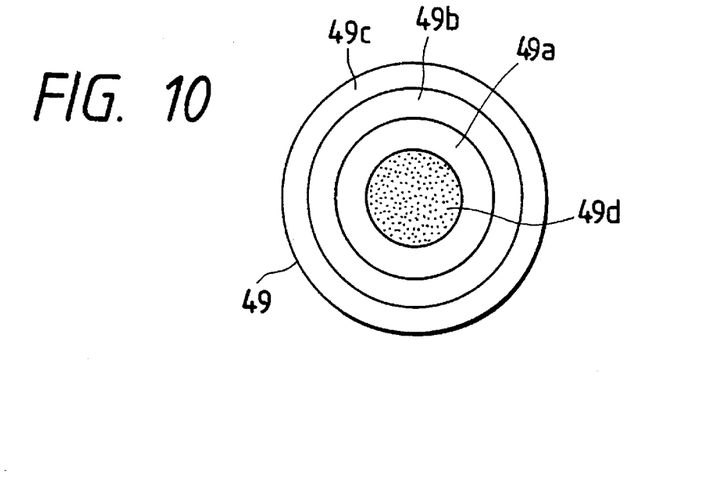
FIG. 10 is a front view of a light beam separating member.
Figure 11:
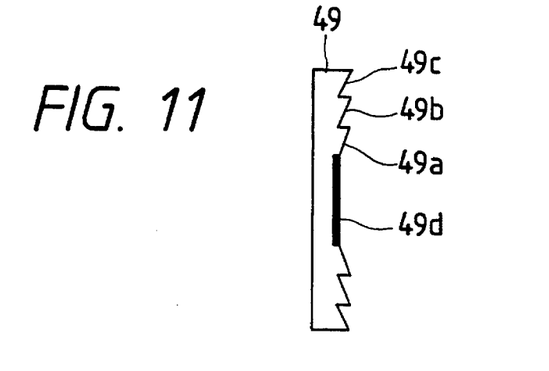
FIG. 11 is a cross-sectional view of the light beam separating member.

The ring aperture stop 43 and the light beam separating member 49 are positioned at conjugate positions with respect to the pupil Ep of the eye E to be examined. The center aperture stop 48 is positioned at a conjugate position with respect to the eye fundus Er. As shown in FIGS. 10 and 11, the light beam separating member 49 consists of three conical prisms 59a to 59c and a shield portion 49d at the center which shields the light beam. The center aperture stop 48 is located at the conjugate position with respect to the light source 41.

The light beam emitted from the light source 41 passes through the lens 42 and the aperture 43a of the ring aperture stop 43, and is reflected by the mirror 44 and the half mirror 45 to be projected through the object lens 46 on the eye fundus Er of the eye E to be examined. The reflected light beam from the eye fundus Er is emitted from the entire pupil Ep, and then, half of them are transmitted through the half mirror. The transmitted light beam passes through the aperture 48a of the center aperture stop 48, the light beam separating member 49 and the lens 50 to be formed on the image pick-up element 51 as ring image R1 to R3 shown in FIG. 12. These ring images R1 to R3 correspond to light beams transmitted through the conical prisms 49a to 49c of the light beam separating member 49, respectively. The eye refraction values are calculated on the basis of the shapes and the size of these ring images.

The interlocking mechanism 52 moves the lenses 42 and 50 and the center aperture stop 48 so that the light source 41 and the image pick-up element 51 come to be positioned substantially at the conjugate positions with respect to the eye fundus Er, so that focusing the ring images R1 to R3 is performed.

Figure 12:
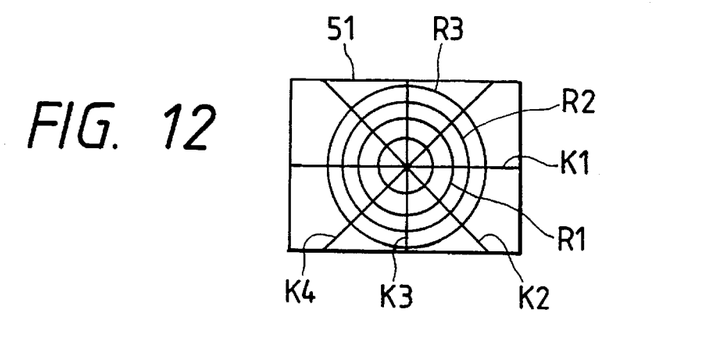
FIG. 12 is an explanatory view of ring images on the image pick-up element.

When measurement is performed at the in-focus position the image signals from the image pick-up element 51 are input to a computer. The eye refraction values are calculated as follows. For example, four meridians K1 to K4 which radially extend from the center, as shown in FIG. 12, are used. Then, the ring images R1 to R3 are approximated as ellipses on the basis of intersections on the meridians K1 to K4 with the ring images R1 to R3. Thus, refractivity of the sphere, the directions of astigmatism and the degree of astigmatism are calculated on the basis of the size of these ellipses and the positions of the lenses 42 and 50.

As shown in FIG. 9, since the reflected light beam on the cornea is not transmitted through the object lens 46 and travels outside of the light receiving system, that is, since the light beam which is useless for measurement is shielded by the center aperture stop 48, useless light which may disturb measurement does not reach the image pick-up element 51. But if the aperture 48a of the center aperture stop 48 at the conjugate position with respect to the light source 41 is too small, the light beam to be measured scatters in the peripheral portion of the aperture 48a and causes errors of measurement. Accordingly the aperture 48a should be large enough to avoid this problem. The center aperture 48 can also improve the clarity of the ring images R1 to R3 on the image pick-up element 51, but is not necessary.

Though the lenses 42 and 50 are driven by the interlocking mechanism 52, they may be fixed as in the prior art. In this case, radial distribution of refractivity on the pupil can be measured by determining eye refraction values on the basis of only the size of the ring images R1 to R3 on the image pick-up element 51.

A point light source as the light source 41 is preferable because the ring images R1 to R3 become fine and are easily separated on the image pick-up element 51, and the refraction at fovea is impossible. In order to increase the amount of received light on the image pick-up element 51, however, the point light source cannot be too small.

The half mirror 45 can be located anywhere on the optical paths from the ring aperture stop 43 to the eye E to be examined. Light beams may be separated by polarization. The image pick-up element 51 may consist of a two-dimensional array sensor, or it may also consist of a plurality of array sensors.

Figure 13:
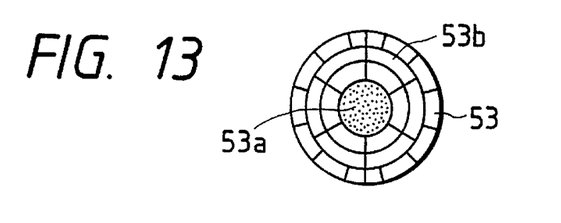
FIG. 13 is a front view of a modified light beam separating member.
Figure 14:
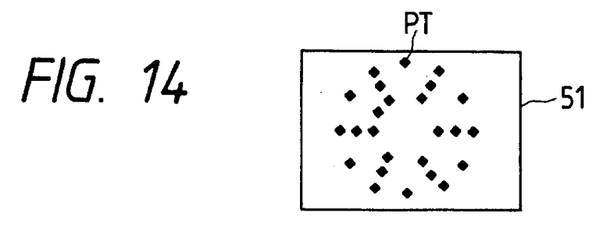
FIG. 14 is an explanatory view of point light beam images on the image pick-up element.

Further, the inverted conical prisms 49a to 49C can be replaced by a light beam separating member 53 consisting of a shield portion 53a at the center and many wedge prisms 53b as shown in FIG. 13. In this case, as shown in FIG. 14, many point light beam images PT are formed on the image pickup element 51. By calculating the positions of the formed images, the eye refractivity values of the parts on the pupil Ep of the eye E to be examined which correspond to respective positions of the formed image can be obtained.

Figure 15:
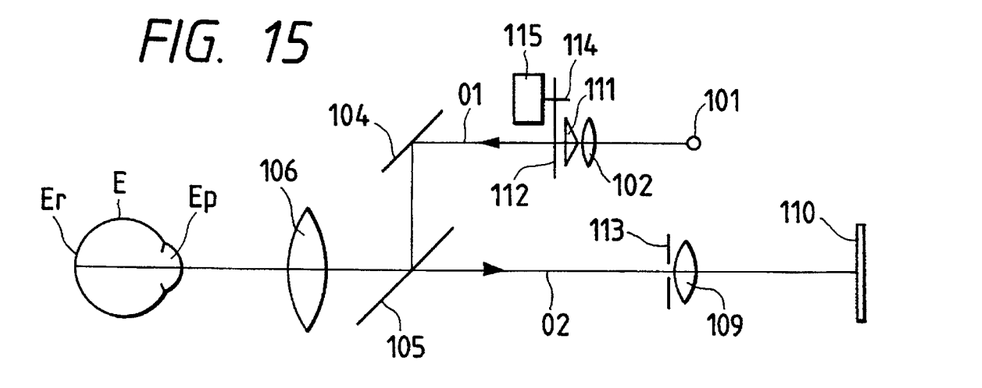
FIG. 15 is an optical layout diagram of the fourth embodiment.
Figure 16:
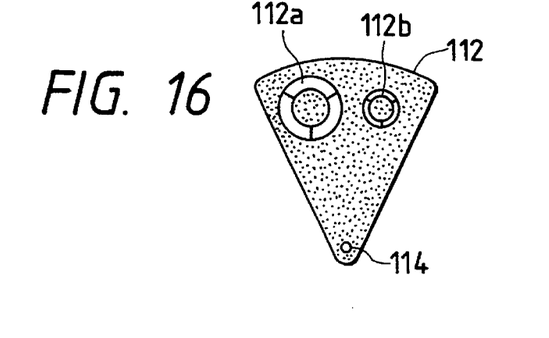
FIG. 16 is an explanatory view of a diaphragm.

FIG. 15 shows the fourth embodiment. On the optical path 01 from a point light source 101 to the eye E to be examined, there are arranged: a lens 102; a mirror 104; a half mirror 105; and an object lens 106, which constitute a projection optical system. The reflection point P of the mirror 104 coincides with a focal position at the rear side of the object lens 106. On an optical path 02 behind the half mirror 105, there are arranged: a lens 109; and an optical position sensor 110 such as a CCD image pick-up element which is located at the conjugate position with respect to an emmetropic eye fundus, thereby constituting a light receiving optical system. Incidentally, the half mirror 105 can be replaced by a wave front dividing member such as a polarizing prism or the like. A conical prism 111 and a ring aperture plate 112 are arranged at the conjugate position with respect to the pupil on the optical path 01 of the projection optical system, while a center aperture stop 113 are arranged at the conjugate position with respect to the pupil on the optical path 02 of the light receiving optical system. The ring aperture plate 112 in the projection optical system has, as shown in FIG. 16, a large ring aperture 112a and a small ring aperture 112b, which are switched to be used according to the diameter of the pupil by rotating an axis 114 of the aperture plate 112 by means of a solenoid 115. The position of the set of conical prism 111 and the ring aperture plate 112 and the position of the center aperture stop 113 can be exchanged.

Though, in this fourth embodiment, an area sensor is employed as the optical position sensor 110, measurement only in one meridian direction can be made by employing a line sensor. Though, in this embodiment, the half mirror 105 is used as the light separating member for separating a projected light beam L1 from a reflected light beam L2 from the eye fundus, a member instead of the half mirror 105 separating by polarization, can be used. This light separating member can be arranged in front of the objective lens 106. In any of the cases described above, since a special optical member such as an apertured mirror is not required in order to separate the projected light beam L1 from the reflected light beam L2 from the eye fundus, the constitution can be simplified. In addition, as the projected light beam L1 and the reflected light beam L2 from the eye fundus need not to be separated on the pupil, the measurement of an eye with small pupil or opacity can be easily performed.

Figure 17:
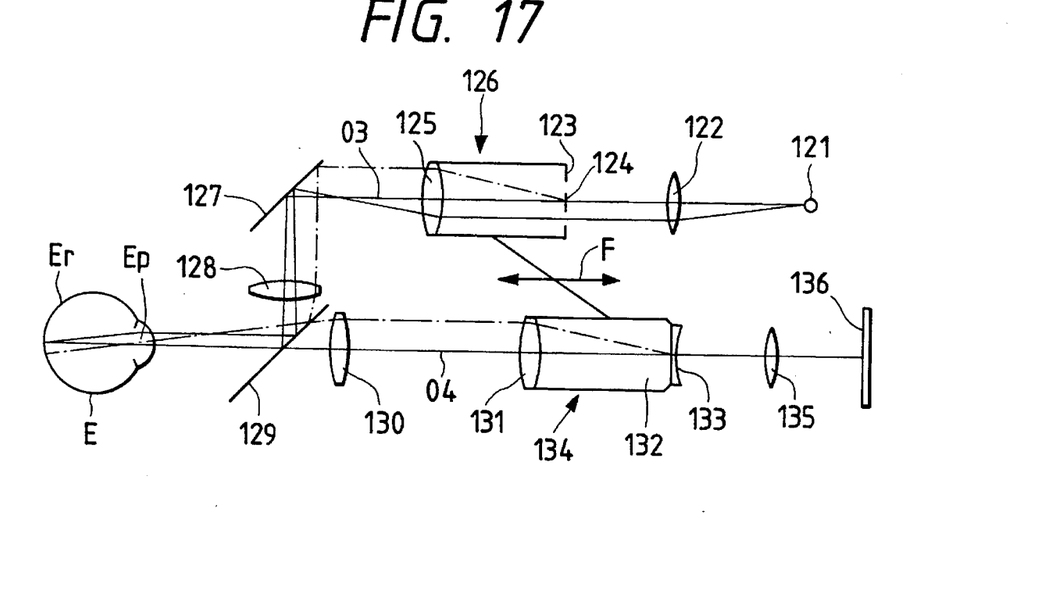
FIG. 17 is an optical layout diagram of the fifth embodiment.

FIG. 17 shows the fifth embodiment. On an optical path 03 from a point light source 121 such as an LED to the eye E to be examined, there are arranged: a lens 122; a focus unit 126 on the projection side consisting of a diaphragm 123 having a shield member 124 on an optical axis and a lens 125 united therewith; a mirror 127; an object lens 128; and a half mirror 129. On an optical path 04 behind the half mirror 129, there are arranged: an object lens 130; a focus unit 134 on the light receiving side which consists of a lens 131, a diaphragm 132 and a separating prism 133 unified together and which is driven simultaneously with the focus unit 126 on the projection side; a lens 135; and a photoelectric array senser 136 such as CCD.

Figure 18A:
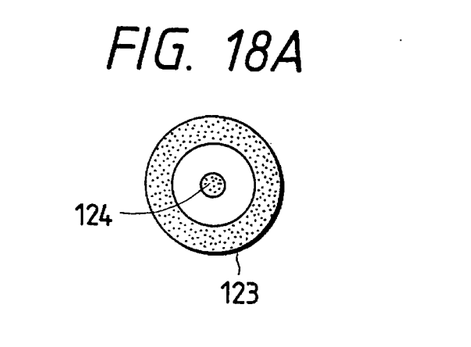
FIGS. 18A and 18B are explanatory views of a pupil-conjugated diaphragm.
Figure 18B:
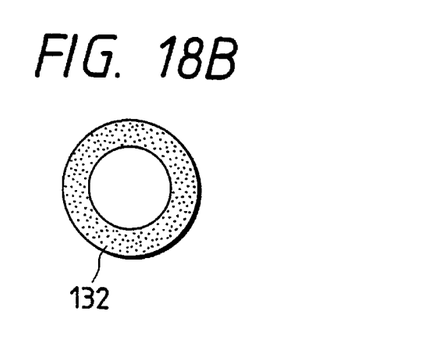

The lens 122 is the same as the lens 135, and the object lens 128 is the same as the object lens 130. And the point light source 121 and the photoelectric array sensor 136 are arranged at conjugate positions from the half mirror 129. The diaphragm 123 shown in FIG. 18A is arranged at a focal point on the rear side of the lens 126, while the diaphragm 132 shown in FIG. 18B is arranged at a focal point on the rear side of the lens 131. The pupil Ep is positioned at a focal position on the front side of the object lenses 128 and 130.

The light beam from the point light source 121 is collimated by the lens 122, passes through the focus unit 126 on the projection side, is reflected by the mirror 127, passes through the object lens 128, and then reflected again by the half mirror 129 to be projected on the eye fundus Er of the eye E to be examined as a spot light beam. Part of the reflected light beam from the eye fundus passes through the half mirror 129, the object lens 130 and further through the lens 131, the diaphragm 132 and the separating prism 133 of the focus unit 134 on the light receiving side, and then is converted into a six spot light beam by the lens 135 to be received on the photoelectric array sensor 136.

Figure 19:
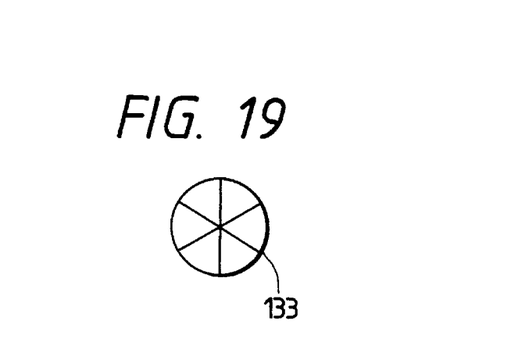
FIG. 19 is an explanatory view of a separating prism.

FIGS. 18A and 18B show the shapes of the diaphragms 123 and 132, respectively. An optical axis shield portion 124 of the diaphragm 123 in the focus unit 126 on the projection side removes the reflected light from the cornea. This optical axis shield portion 124 can be provided in the diaphragm 132 on the light receiving side. The separating prism 133 shown in FIG. 19 consists of six wedge prisms which are symmetrically arranged with respect to the optical axis and which divide the light beam by each of the meridians.

Figure 20:
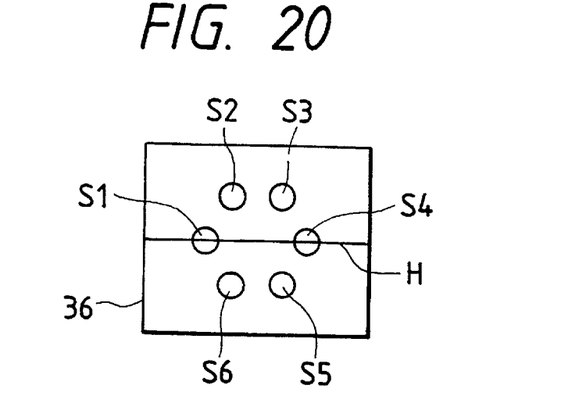
FIG. 20 is an explanatory view of reflected light beams from an eye fundus on a photoelectric array sensor.

Accordingly, six spot light beams S1 to S6 are received on the photoelectric array sensor 136, as shown in FIG. 20. The focus unit 126 on the projection side and the focus unit 134 on the light receiving side are simultaneously removed in the directions of respective optical axes as indicated by the arrow F in the figure and are brought to an in-focus position so that the point light source 121 and the photoelectric array sensor 136 come to conjugate positions with respect to the eye fundus Er. Then, the eye refraction values are calculated by a computer on the basis of the positions of the focus units 126 and 134 and the positions of the spot light beams S1 to S6 on the photoelectric array sensor 136.

When in focus, the distance between the spot light beams S1 and S4 on the photoelectric array sensor 136 varies linearly with respect to refraction diopters of the eye E to be examined. In actual measurement, for example, signals on the line H are being monitored during focusing movement, which is stopped when the positions of the two spot light beams is i the sharpest. Then, positions of the six spot light beams S1 to S6 are calculated to obtain eye refraction values including astigmatism.

When the eye has astigmatism, the spots other than focused ones are somewhat out of focus. The position of a spot is calculated by using the gravity of light in the spot. Distances between the other two pairs of spots, against in-focus horizontal pair of spots also vary linearly according to a change in the diopters of the eye.

This embodiment is, different from the conventional apparatus in that the calculation of the refractivity of the eye can be executed on the basis of not only the positions of the focus lenses but also the positions of the spots. Therefore high precision can be obtained even when the focusing is not so precise.

Incidentally, the separating prism 133 shown in FIG. 17 can be replaced by a conical prism. In this case, a ring shaped light beam is obtained and its shape is analyzed. Also, the separating prism 133 may be located in the vicinity of the diaphragm 123 on the projection side. In this case, six spots are projected on the eye fundus.

If the diameter of the diaphragm 123 is very small, for example not more than 1 mm, images at the fundus blur a little. So, the projection optical system has no need to be moved for focusing. In this case, only the light receiving side is focused. The half mirror 129 in FIG. 17 may be replaced by a prism. In this case, the surface thereof is slanted to bend the reflect light outwards. When a prism is arranged behind the object lenses 128 and 130, a common object lens can be used. In this case, however, some countermeasure against surface reflection caused thereby must be taken.

Figure 21:
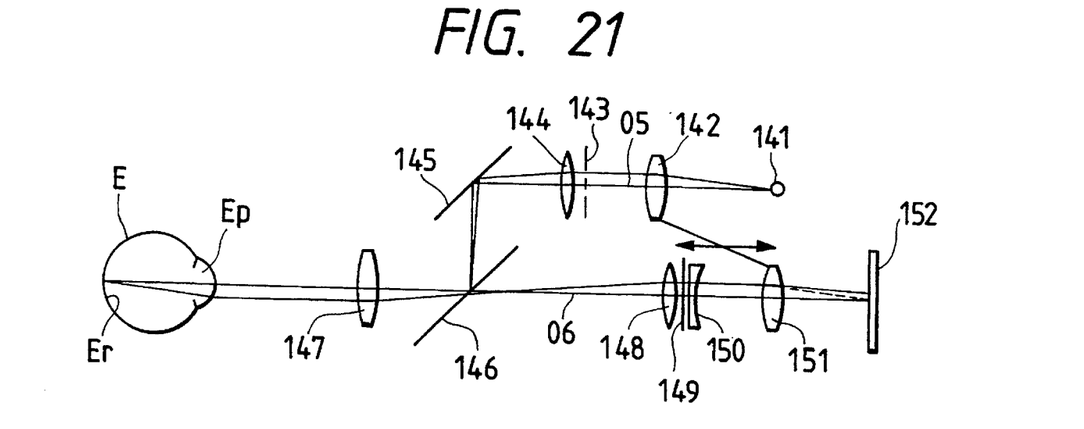
FIG. 21 is an optical layout diagram of the sixth embodiment.

FIG. 21 shows the sixth embodiment. On an optical path 05 from a point light source 141 to the eye E to be examined, there are arranged: a focus lens 142; a diaphragm 143; a lens 144; a mirror 145; a half mirror 146; and an object lens 147. On an optical path 06 behind the half mirror 146, there are arranged: a lens 148; a diaphragm 149; a separating prism 150; a focus lens 151 which is united with the focus lens 142; and a photoelectric sensor array 152. The diaphragm 143 on the projection side and the diaphragm 149 on the light receiving side are arranged at conjugate positions with respect to the pupil Ep.

In this constitution, the light beam from the point light source 141 passes through the focus lens 142, the diaphragm 143, the lens 144, the mirror 145, the half mirror 146 and the object lens 147 to be projected on the eye fundus Er of the eye E to be examined. The reflected light beam from the eye fundus passes through the object lens 147, the half mirror 146, the lens 148, the diaphragm 149, the separating prism 150 and the focus lens 151 to be received by the photoelectric array-sensor 152.

The lenses 144 and 148 collimate the light beam, thereby balancing the changes of spot light beams on the photoelectric array sensor 152 with respect to plus end diopter and minus end diopter. The focus lenses 142 and 151 are integrally moved along respective optical axes so that the point light source 141 and the photoelectric array sensor 152 come to conjugate positions with respect to the eye fundus Er. The way that the eye refraction values are obtained on the basis of the positions of the six spots on the photoelectric array sensor 52 and the positions of the focus lenses is the same as in the embodiment shown in FIG. 17. As to the distance between a pair of focused spots, the positions of respective spots on plus and minus sides change by the same amount in the same direction. But the change in distance is not linear with respect to the diopter.

Yet, when the focus lenses are arranged at certain positions, the distance between the spots varies linearly with respect to the change in diopters. Therefore, in the same way as in the embodiment shown in FIG. 17, the eye refraction values can be calculated on the basis of the distances between other spots, that is, two pairs of spots, wherein the systems are focused so as to bring the two spots on the horizontal line into focus.

Incidentally, the separating prism 150 may be located in the vicinity of the diaphragm 143 on the projection side. And when a light beam on one side is thin enough, in-focus operation is not necessary. In the embodiments shown in FIGS. 17 and 21, precise measured values can be obtained, as the measurement can be made by the light beam passing the entire area of the pupil.

What is claimed is:

1. An eye refraction measuring apparatus comprising:

a projection system for projecting a light beam to be used for measurement comprising at least one optical member;

a light receiving optical system comprising at least one optical member and having a light detecting element;

an optical path separating member through which said projection system projects the light beam to be used for measurement on the eye to be examined, and through which said light receiving system leads the reflected light beam from the eye to be examined to said light detecting element, and which reduces the intensity of the reflected light beam by dividing the reflected light beam; and a mobile mechanism for moving at least one optical member of at least one of said projection system and said light receiving optical system, wherein the eye refraction values are measured on the basis of the position of the at least one optical member moved by said mobile mechanism and the detection of said light detecting element at said position.

2. An eye refraction measuring apparatus according to claim 1, wherein said projection system and said light receiving system have respective diaphragms at conjugate positions with respect to the anterior part of the eye to be examined.

3. An eye refraction measuring apparatus according to claim 1, wherein said mobile mechanism moves said at least one optical member of said projection system together with said at least one optical member of said light receiving member.

4. An eye refraction measuring apparatus according to claim 1, wherein said projection system has a diaphragm member at a conjugate position with respect to the anterior part of the eye to be examined, and said diaphragm member has an aperture at a position eccentric with respect to an optical axis.

5. An eye refraction measuring apparatus according to claim 1, wherein said light receiving system has a light beam separating member at a conjugate position with respect to the pupil of the eye to be examined, wherein said light beam separating member separates a light beam into a plurality of light beams at different distances from an optical axis, and the refractivity of the eye at different portions of the pupil of the eye to be examined are measured on the basis of positions of the light beams on said light detecting element.

6. An eye refraction measuring apparatus according to claim 1, wherein said light receiving system has:

a lens;

a diaphragm arranged at a focal position at the rear side of said lens;

a prism which refracts the light beam in a direction vertical with respect to an optical axis; and a focus unit which can be moved by said mobile mechanism in two directions along the optical axis.

7. An eye refraction measuring apparatus according to claim 1, wherein said light receiving system has a focus lens which is movable in two directions along an optical axis and a prism which refracts the light beam in a direction vertical with respect to the optical axis, and wherein the eye refraction values of the eye to be examined are measured on the basis of the position of said focus lens and the positions of the light beams on said light detecting element.

8. An eye refraction measuring apparatus comprising:

a projection system for projecting a light beam to be used for measurement;

a light receiving optical system having a light detecting element;

an optical path separating member through which said projection system projects the light beam to be used for measurement on the eye to be examined, and through which said light receiving system leads the reflected light beam from the eye to be examined to said light detecting element, and which reduces the intensity of the reflected light beam by dividing the reflected light beam; and a light beam separating member which is provided at a conjugate position in said light receiving system with respect to the pupil of the eye to be examined in order to separate a light beam into a plurality of light beams at different distances from an optical axis, wherein the eye refraction values of respective portions of the pupil of the eye to be examined are measured on the basis of the positions of light beams on said light detecting element.

9. An eye refraction measuring apparatus according to claim 8, wherein said light beam separating member has a plurality of conical prisms arranged concentrically.

10. An eye refraction measuring apparatus according to claim 8, wherein said light beam separating member has a plurality of concentric wedge prisms.

11. An eye refraction measuring apparatus comprising:

a projection system for projecting a light beam to be used for measurement;

a light receiving optical system having a light detecting element wherein the eye refraction values are measured on a basis of the results detected by said light detecting element;

an optical path separating member through which said projection system projects the light beam to be used for measurement on the eye to be examined, and through which said light receiving system leads the reflected light beam from the eye to be examined to said light detecting element, and which reduces the intensity of the reflected light beam by dividing the reflected light beam; and a diaphragm member which is provided in one of said projection system and light receiving system, and which has a ring-shaped aperture whose size can be changed on the optical path in the projection system.

12. An eye refraction measuring apparatus according to claim 11, wherein said diaphragm member has a plurality of ring-shaped apertures of different diameters so as to alternately insert said plurality of ring-shaped apertures in the optical path in said projection system.

13. An eye refraction measuring apparatus comprising:

an optical system for projecting a light beam to be used for measurement onto a fundus of an eye to be examined, and for leading a light beam from the fundus of the eye to be examined to a light detecting element; and a light beam separating member which is provided at the position conjugate to the pupil of the eye to be examined in an optical path of said optical system in order to separate a light beam into a plurality of light beams at different distances from an optical axis of said optical system, wherein the eye refraction values of respective portions of the pupil of the eye to be examined are measured on the basis of the positions of light beams separated by said light beam separating member on said light detecting element.

14. An eye refraction measuring apparatus comprising:

an optical system for projecting a light beam to be used for measurement onto a fundus of an eye to be examined, and for leading a light beam from the fundus of the eye to be examined to a light detecting element, the eye refraction values being measured on the basis of the detection of the light detecting element; and light beam diameter changing means which is provided at a position conjugate to the pupil of the eye to be examined in an optical path of said optical system in order to change a diameter of a light beam with respect to the distance from an optical axis of said optical system.

* * * * *

UNITED STATES PATENT AND TRADEMARK OFFICE
CERTIFICATE OF CORRECTION

PATENT NO. : 5,523,809
DATED : June 4, 1996
INVENTOR(S) : YOSHIMI KOHAYAKAWA

It is certified that error appears in the above-indentified patent and that said Letters Patent is hereby corrected as shown below:

ON THE COVER PAGE & COLUMN 1, LINE 3,

[54] TITLE,
    Line 3, "MEMBER" should read --MEMBER,--.

[57] ABSTRACT,
    Line 1, "ophtalmology" should read --ophthalmology--.
    Line 4, "apertured-mirror." should read --apertured mirror.--.
    Line 5, "a" should be deleted.
    Line 7, "distribution" should read --the distribution--.

COLUMN 1
    Line 3, "MEMBER" should read --MEMBER,--.

COLUMN 2
    Line 64, "inversed" should read --inverse--.

UNITED STATES PATENT AND TRADEMARK OFFICE
CERTIFICATE OF CORRECTION

PATENT NO. : 5,523,809
DATED : June 4, 1996
INVENTOR(S) : YOSHIMI KOHAYAKAWA

It is certified that error appears in the above-indentified patent and that said Letters Patent is hereby corrected as shown below:

COLUMN 3

Line 39, "high" should read --high peaks--, and "signal 52." should read --signal S2.--.

Line 51, "inversed" should read --inverse--.

COLUMN 4

Line 45, "mates" should read --make--.

Line 60, "stigmatism" should read --astigmatism--.

COLUMN 5

Line 24, "them are" should read --it is--.

COLUMN 6

Line 17, "49C" should read --49c--.

Line 43, "are" should read --is--.

Line 67, "to" should be deleted

UNITED STATES PATENT AND TRADEMARK OFFICE
CERTIFICATE OF CORRECTION

PATENT NO. : 5,523,809
DATED : June 4, 1996
INVENTOR(S) : YOSHIMI KOHAYAKAWA

It is certified that error appears in the above-indentified patent and that said Letters Patent is hereby corrected as shown below:

COLUMN 7
Line 15, "senser 136" should read --sensor 136--.
Line 65, "i" should be deleted.

COLUMN 8
Line 6, "diopters" should read --diopter--.
Line 7, "is," should read --is--.
Line 48, "array-sensor" should read --array sensor--.

COLUMN 9
Line 58, "are" should read --is--.

Signed and Sealed this

Twelfth Day of November, 1996

Attest:

BRUCE LEHMAN

Attesting Officer    Commissioner of Patents and Trademarks